United States Patent [19]

AF Ekenstam et al.

[11] 4,302,465
[45] Nov. 24, 1981

[54] THERAPEUTICALLY ACTIVE, SUBSTITUTED PIPERIDINES AND PYRROLIDINES THERAPEUTIC COMPOSITIONS THEREOF AND METHODS OF USE THEREOF

[76] Inventors: Bo T. AF Ekenstam, Box 721, Hjälteby, Sweden, S-440 74; Gunnar A. K. Aberg, Utsiktsvägen 7, Falkenberg, Sweden, S-311 00

[21] Appl. No.: 97,148

[22] Filed: Nov. 26, 1979

[30] Foreign Application Priority Data

Oct. 7, 1979 [SE] Sweden ............................ 7906000

[51] Int. Cl.³ .................. A61K 31/40; A61K 31/445; C07D 204/14; C07D 211/58
[52] U.S. Cl. .................................... 424/267; 424/274; 546/225; 260/326.47
[58] Field of Search ................... 260/326.47; 546/225; 424/267, 274

[56] References Cited

U.S. PATENT DOCUMENTS

| | | | |
|---|---|---|---|
| 2,792,399 | 5/1957 | Ekenstam et al. | 546/225 |
| 2,799,679 | 7/1957 | Ekenstam et al. | 546/225 |
| 4,110,331 | 8/1978 | Pettersson | 546/225 |

FOREIGN PATENT DOCUMENTS

| | | |
|---|---|---|
| 161236 | 11/1957 | Sweden . |
| 161237 | 11/1957 | Sweden . |
| 161519 | 12/1957 | Sweden . |
| 164062 | 7/1958 | Sweden . |
| 164063 | 7/1958 | Sweden . |
| 164674 | 9/1958 | Sweden . |
| 191321 | 9/1964 | Sweden . |
| 191322 | 9/1964 | Sweden . |
| 192045 | 10/1964 | Sweden . |
| 487152 | 4/1970 | Switzerland . |

OTHER PUBLICATIONS

Chemical Abstracts, vol. 86, Item 121082n, (1977), Abstracting, Tsuge et al., in Bull. Chem. Soc., Japan, (1976), vol. 49, No. 10, pp. 2828–2832.
Bouche et al., "Pharm. Acta. Helv.," (1976), vol. 51, Nos. 7–8, pp. 223–235.

*Primary Examiner*—Robert T. Bond
*Attorney, Agent, or Firm*—Brumbaugh, Graves, Donohue & Raymond

[57] ABSTRACT

A compound of formula

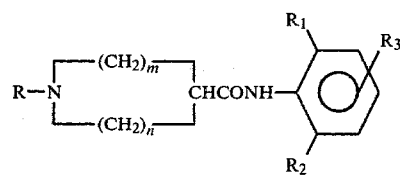

in which
m and n are a pair of integers such that m=0 or 1 and n=3−m or m=0, 1 or 2 and n=4−m, R is straight or branched $C_2$ to $C_4$ alkyl having a terminal hydroxy group,
$R_1$ is methyl or methoxy,
$R_2$ is methyl or ethyl and
$R_3$ is hydrogen or methyl;

or a pharmaceutically acceptable salt thereof is provided, as well as compositions containing these compounds and processes for preparing them. The compounds can be used to produce topical and local anaesthetic effects in mammals and are also useful as heart anti-arrhythmic agents.

23 Claims, No Drawings

THERAPEUTICALLY ACTIVE, SUBSTITUTED PIPERIDINES AND PYRROLIDINES THERAPEUTIC COMPOSITIONS THEREOF AND METHODS OF USE THEREOF

The present invention relates to new chemical compounds, methods of manufacturing them, pharmaceutical preparations containing these substances and methods of treatment using these compounds in order to produce local anaesthetic, topical anaesthetic and anti-arrhythmic effects in mammals.

The membrane stabilizing substances lidocaine and mepivacaine have been clinically used both as local anaesthetics and as anti-arrhythmic agents for the heart. The usefulness of lidocaine and mepivacaine is, however, limited by the toxic properties of the substances, in particular by their general toxicity and their tissue toxicity when the substances are used as local anaesthetics, and their general toxicity when the substances are used as anti-arrhythmic agents for the heart.

The present invention relates to new substances which, in experiments performed on animals, have been found to have a better therapeutic index, that is a therapeutic margin, than lidocaine and mepivacaine.

The present invention provides compounds of formula I below in the form of racemates or their optically active isomers:

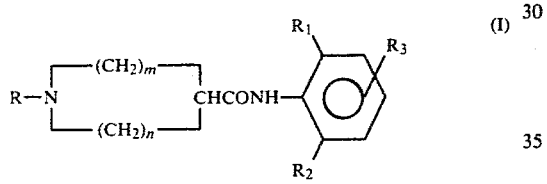

(I)

in which R is a straight or branched alkyl residue containing 2 to 4 carbons and a terminal hydroxy group, $R_1$ is selected from the group consisting of methyl and methoxy, $R_2$ is selected from the group consisting of methyl and ethyl, $R_3$ is selected from the group consisting of hydrogen and methyl and m and n are a pair of integers such that $m=0$ or $1$ and $n=3-m$ or $m=0, 1$ or $2$ and $n=4-m$.

The compounds may alternatively be in the form of pharmaceutically acceptable salts.

In formula I, R may be, for example selected from the group consisting of 2-hydroxyethyl, 3-hydroxypropyl, 4-hydroxybutyl, 2-hydroxy-1-methylethyl, 3-hydroxy-1-methylpropyl, 3-hydroxyl-2-methylpropyl, quaternary 2-hydroxyethyl-N-methyl, quaternary 3-hydroxy-1-methylproply-N-methyl, quaternary 3-hydroxypropyl-N-methyl, quaternary 2-hydroxyethyl-N-ethyl and quaternary 3-hydroxyproply-N-ethyl.

Examples of compounds of the present invention are as follows:

N-(2-Hydroxyethyl)pipecolinyl-2,6-dimethylanilide

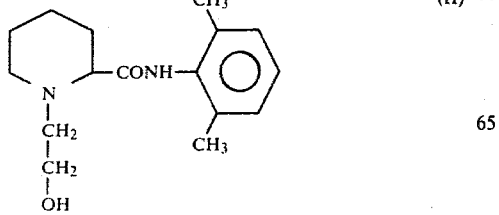

(II)

N-(2-Hydroxyethyl)pipecolinyl-2,4,6-trimethylanilide

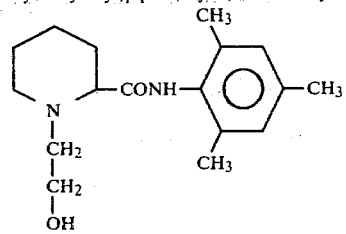

(III)

N-(3-Hydroxypropyl)pipecolinyl-2,6-dimethylanilide

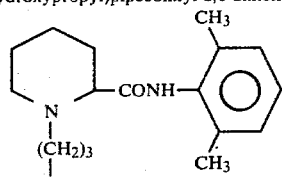

(IV)

N-(2-Hydroxyethyl)pipecolinyl-2-methoxy-6-methylanilide

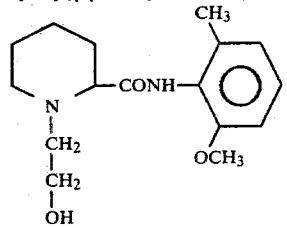

(V)

N-(4-Hydroxybutyl)-isopipecolinyl-2,4,6-trimethylanilide

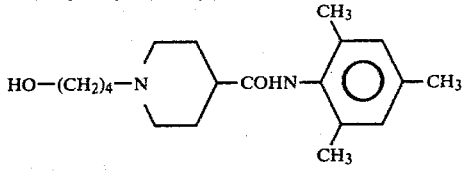

(VI)

N-(2-Hydroxy-1-methylethyl)prolyl-2,6-dimethylanilide

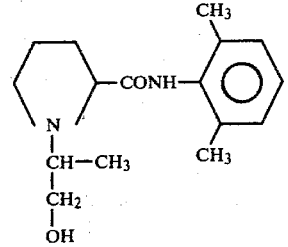

(VII)

N-(Quaternary-2-hydroxyethyl-N-methyl)pipecolinyl-2,6-dimethylanilide

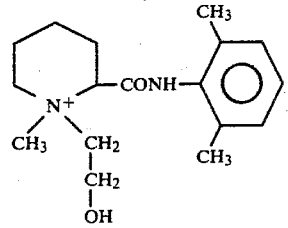

(VIII)

N-(2-hydroxyethyl)prolyl-2,6-dimethyl-anilide

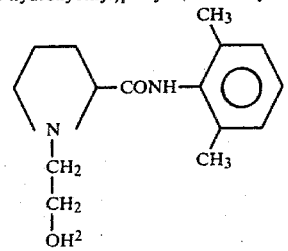

(IX)

METHOD A

A pyridine or pyrrole carboxylic acid anilide (a) is hydrogenated to the corresponding piperidine or pyrrolidine carboxylic acid anilide (b) which is thereafter hydroxy-alkylated to form a compound in accordance with formula I. $R_1$, $R_2$ and $R_3$ in (a) and (b) are as defined in Formula I.

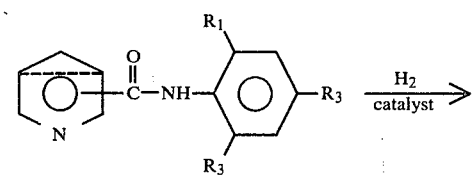

(a) (c)

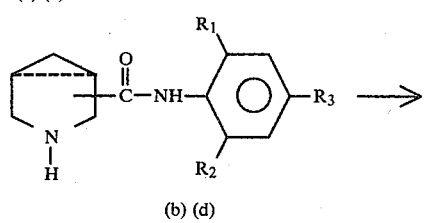

(b) (d)

The formula

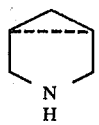

is used herein to designate that either the corresponding piperidine 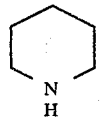 or pyrrolidine 

compound can be used.

The formula

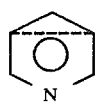

is used herein to designate that either the corresponding pyridine or pyrrole compound can be used.

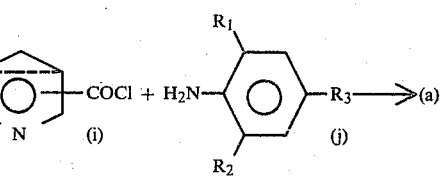

METHOD B

Compounds of formula (a) can alternatively be produced by reacting a pyridine or pyrrole carboxylic acid chloride (i) with an aromatic amide (j)

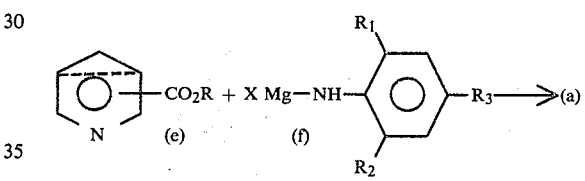

or by reacting a pyridine or pyrrole carboxylic acid ester (e) with a metal organic derivative of an aromatic amine (f)

wherein X=halogen and $R_1$, $R_2$ and $R_3$ in (d) and (f) are defined as in formula I.

METHOD C

The compounds of formula I can also be produced by reacting a piperidine or pyrrolidine carboxylic acid (g) with an aromatic amine (d) or the corresponding isocyanate (h) to form a compound of type (b) identified above which can then be hydroxyalkylated to form a substance in accordance with formula I.

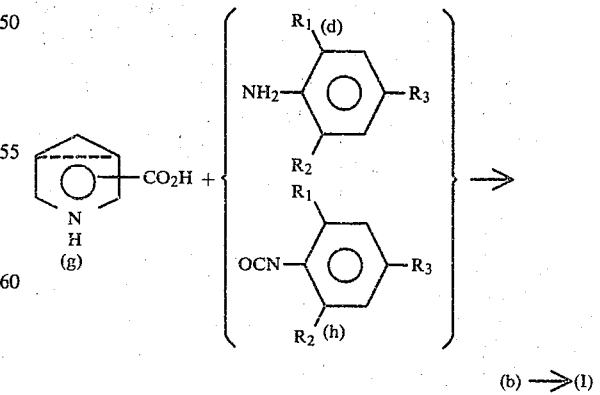

An acid of type (g) may first be converted to a more reactive derivative, such as an acid chloride (i), an acid anhydride or an ester (e), whereupon the derivative thus produced is caused to react with the aromatic amine (d) or the aromatic isocyanate (h) after which the compound of type (b) obtained is converted to a compound in accordance with formula I by means of hydroxy-alkylation.

Other methods of producing compounds of formula I, or intermediate products which could be converted to compounds of formula I, apart from those illustrated in Methods A–C above, may also be used. Alternative methods of preparation are described for example in Swedish Pat. Nos. 161236, 161237, 161519, 164062, 164063, 164674, 191321, 191322 and 192045 which are incorporated herein by reference.

In order to produce the compounds of the present invention by the methods described in the Swedish patent specifications, the N-alkylation process must be modified so that the alkylation agent contains at least one reactive hydroxylalkyl group or group which can be transformed in a simple operation to a hydroxyalkyl group, such as by means of hydrolysis. The most suitable alkylation agents are halogen alkyl hydrines, hydroxyalkyl sulphates, hydroxyalkyl sulphonates, alkyl anoxides or dihalogen hydrocarbons. The N-hydroxyalkyl compounds of the present invention can be produced as the final process step, if necessary by hydroxyalkylation of corresponding pyrrole or pyridine carboxy aryl amides followed by hydration in accordance with the procedure described in the Swedish Patent Specifications cited above.

Stereoisomers of the optically active amides can be manufactured by using the optically active pyrrolidine or piperidine carboxylic acid which, through further synthesis, gives the optically active final product desired. Alternatively the optically active steroisomers can be separated out by forming salts with optically active acids.

The following Examples serve to illustrate the synthesis of a selection of compounds of the present invention.

EXAMPLE 1

DL-N-(2-hydroxyethyl)pipecolinyl-2,6-dimethylanilide HCl 11 g of D,L-piperidine-α-carboxy-2,6-dimethylanilide is dissolved in 150 ml pure alcohol, placed in a 200 ml autoclave, an cooled down to −60° C. 4 g ethylene oxide is added and caused to react in the closed autoclave for 24 hours at room temperature. The alcohol is then evaporated off and the remaining distillate is obtained in the form of a yellow oil. This oil is then fully dissolved, without previous purification, in 100 ml methyl ethyl ketone and the requisite amount of dry HCl gas is added. The hydrochloride of DL-N-(2-hydroxyethyl)pipecolinyl-2,6-dimethylanilide (see formula II) is crystallized out with the aid of graft crystals. 11 g final product was obtained having a melting point 247°–248° C. Equivalent weight 313.3 (theoretical weight 312.8).

EXAMPLE 2

DL-N-(2-hydroxyethyl)pipecolinyl-2,6-dimethylanilide HCl 23.1 g of D,L-piperidine-α-carboxy-2,6-dimethylanilide is dissolved in 100 ml pure alcohol and mixed in a sealed reactor with 10 g potassium carbonate and 5 g 2-bromine-ethyl hydrine after which the mixture is slowly heated to boiling point over 10–12 hours. The mixture is filtered to remove potassium bromide and excess carbonate formed at 60° C. and washed with 20 ml heated, pure alcohol. The cleaning and filtering is performed with about 3 g active carbon and the alcohol evaporated off. The distillation residue consists of about 25 g DL-N-(2-hydroxyethyl)pipecolinyl-2,6-dimethylanilide (II) which is converted to the hydrochloride in accordance with Example 1 by dissolving the residue in ethyl methyl ketone and introducing dry HCl gas. The purified final product has a melting point of 247°–248° C.

EXAMPLE 3

N-(3-Hydroxypropyl)-pipecolinyl-2,6-dimethylanilide 12 g D,L-piperidine-2-carboxy-2,6-dimethylanilide is dissolved in 100 ml pure alcohol and mixed in a sealed reactor with 10 g potassium carbonate and 6 g 3-bromine propanol. It is then reacted as described in Example 2. 10 g purified N-(3-Hydroxypropyl)-pipecolinyl-2,6-dimethylanilide is obtained, from which the hydrochloride is produced. The product has a melting point of 258° C.

EXAMPLE 4

The procedure of Example 1 or 2 is used to produce the optically active stereoisomers. The starting material is either the D(−)- or L(+)-amides instead of racemic, D,L-piperidine-α-carboxy-2,6-dimethylanilide. A final product corresponding to D(−)- or L(+)-N-(2-hydroxyethyl)-pipecolinyl-2,6-dimethylanilide hydrochloride is obtained and has an optical activity of $[\alpha]_D^{25}$ and +19°5' for the D(−) and L(+) forms. The L(+) form has a melting point of 217° C.

EXAMPLE 5

N-(quaternary-2-hydroxyethyl-N-methyl)pipecolinyl-2,6-dimethylanilide 15 g N(2-hydroxyethyl)pipecolinyl-2,6-dimethylanilide (base) and 15 g methyl iodide is reflux in 150 ml boiling acetonitrile for 1 hour. After evaporation and stirring with a glass rod a crystalline residue is obtained which is washed with acetone. The final product consists of 13.5 g N-(quaternary-2-hydroxyethyl-N-methyl)pipecolinyl-2,6-dimethylanilide (VIII) which has a melting point of 157° C.

Table 1 lists the properties of some compounds in accordance with the present invention.

TABLE 1

| No. | R | Amide binding | $R^1$ | $R^2$ | $R^3$ | Stereo isomers | M.P °C. HCl salt | Structure verified with NMR |
|---|---|---|---|---|---|---|---|---|
| 1. | HO(CH$_2$)$_2$ | α | CH$_3$ | CH$_3$ | H | DL | 247–248 | X |
| 2. | " | α | CH$_3$ | CH$_3$ | H | L | 192–197 | X |
| 3. | " | α | CH$_3$ | CH$_3$ | H | D | 197 | X |
| 4. | " | α | CH$_3$ | CH$_3$O | H | DL | 245 | X |
| 5. | HO(CH$_2$)$_3$ | α | CH$_3$ | CH$_3$ | H | DL | 258 | X |

TABLE 1-continued

| No. | R | Amide binding | R¹ | R² | R³ | Stereo isomers | M.P °C. HCl salt | Structure verified with NMR |
|---|---|---|---|---|---|---|---|---|
| 6. | HO(CH₂)₂ | α | CH₃O | H | H | DL | 189.5 | X |
| 7. | " | α | CH₃ | H | CH₃ | DL | 229 | X |
| 8. | HO(CH₂)₃ | β | CH₃ | CH₃ | H | DL | 200 | X |
| 9. | HO(CH₂)₂ | λ | CH₃ | CH₃ | H | — | 184 | X |
| 10. | CH₃ and HO(CH₂)₂ | α | | | | DL | 157 | X |

Biological Effects

A.
N-(2-hydroxyethyl)N-(2-hydroxyethyl)pipecolinyl-2,6-dimethylanilide

N-(2-hydroxyethyl)pipecolinyl-2,6-dimethylanilide (II) which is sometimes referred to herein as S-1249 has been found to have an $LD_{50}$ value of 57 mg/kg (lidocaine 28 mg/kg and mepivacaine 31 mg/kg) in experiments with mice (NMRI, ♂ 22–25 g).

S-1249 produced convulsions in experiments with conscious rats when 103±8 mg/kg was given intraveneously (5.0 mg/mg/min; N=10. The letter N is used herein to indicate the number of injections given. In parallel experiments similar convulsions occurred with 39±2 mg/kg (N=10) using lidocaine and 38±3 mg/kg (N=10) using mepivacaine. In experiments on rabbits, S-1249 has been found to cause considerably less tissue irritation using the trypan-blue test than lidocaine and mepivacaine after intracutinous injection as can be seen from the results in Table 2.

TABLE 2

| Substance | Concentration in % and number of injection (N) | Diameter of irratated zone (mm) |
|---|---|---|
| S-1249 | 1.0% (N = 6) | 0.0 |
| | 2.0% (N = 6) | 0.0 |
| | 4.0% (N = 6) | 0.0 |
| | 8.0% (N = 6) | 3.9 |
| Lidocaine | 1.0% (N = 3) | 0.0 |
| | 2.0% (N = 3) | 0.0 |
| | 4.0% (N = 3) | 3.3 |
| Mepivacaine | 1.0% (N = 4) | 0.0 |
| | 2.0% (N = 4) | 0.0 |
| | 4.0% (N = 6) | 0.0 |
| | 8.0% (N = 4) | 7.8 |

In experiments on guinea pigs, S-1249 has been found to have a local anaesthetic effect of the same order of magnitude as lidocaine and mepivacaine after intracutaneous infiltration, as can be seen from the results in Table 3.

TABLE 3

| Substance | Concentration | Number of animals | Duration of Anaesthesia (min) |
|---|---|---|---|
| S-1249 | 1.0% + adrenaline 5 μg/ml | 12 | 140 ± 8 |
| Lidocaine | 1.0% + adrenaline 5 μg/ml | 12 | 132 ± 7 |
| Mepivacaine | 1.0% + adrenaline 5 μg/ml | 12 | 152 ± 16 |

In experiments with rats, S-1249 has been found to have an equivalent local anaesthetic effect to lidocaine and mepivacaine after perineuronal injection close to the sciatic nerve, as can be seen from the results in Table 4.

TABLE 4

| Substance | Concentration | Number of animals | Duration of anaesthesia (min) Sensory Blockage | Motoric Blockage |
|---|---|---|---|---|
| S-1249 | 1.0% + adr. 5 μg/ml | 10 | 82 ± 6 | 83 ± 6 |
| Lidocaine | 1.0% + adr. 5 μg/ml | 10 | 77 ± 5 | 79 ± 5 |
| Mepivacaine | 1.0% + adr. 5 μg/ml | 10 | 87 ± 4 | 89 ± 4 |

In experiments with anaesthetized dogs, S-1249 has been found to have effects equivalent to lidocaine and better than mepivacaine against arrhythmic heart-beats induced by ouabain, as can be seen from the results in Table 5:

TABLE 5

| Substance | Dose (mg/kg) | Number of animals | Number of regularized arrhythmias | Duration of regularization (min) |
|---|---|---|---|---|
| S-1249 | 1.0 | 20 | 13 (65%) | 130 ± 40 |
| | 2.0 | 24 | 17 (70%) | 280 ± 70 |
| Lidocaine | 1.0 | 20 | 12 (60%) | 135 ± 50 |
| | 2.0 | 24 | 19 (79%) | 220 ± 30 |
| Mepivacaine | 1.0 | 10 | 5 (50%) | 110 ± 20 |
| | 2.0 | 12 | 6 (50%) | 185 ± 50 |

In view of its low toxicity, the substance S-1249 has considerably greater therapeutic potential than lidocaine or mepivacaine, both as local anaesthetic and as heart arrhythmic agent.

B.
N-(3-Hydroxypropyl)pipecolinyl-2,6-dimethylanilide

N-(3-Hydroxypropyl)pipecolinyl-2,6-dimethylanilide (IV) herein sometimes referred to as S-1265 has been found to have an $LD_{50}$ value (IV) of 40 mg/kg (lidocaine 28 mg/kg and mepivacaine 31 mg/kg) in experiments with mice (NMRI, ♂ 22–25 g).

In experiments on conscious rats, S-1265 gave CNS effects (convulsions) when 80±4 mg/kg was administered intravenously (5.0 mg/kg/min; N=10). In parallel experiments, similar convulsions occurred when using 39±2 mg/kg (N=10) lidocaine and 38±3 mg/kg (N=10) mepivacaine.

In experiments on guinea-pigs, S-1265 proved to have better local anaesthetic effect than lidocaine after intracutaneous infiltration, as can be seen from the results in Table 6:

TABLE 6

| Substance | Concentration | Number of animals | Duration of anaesthesia (min) |
|---|---|---|---|
| S-1265 | 1.0% + adrenaline 5 μg/ml | 12 | 151 ± 6 |
| Lidocaine | 1.0% + adrenaline 5 μg/ml | 12 | 132 ± 7 |
| Mepivacaine | 1.0% + adrenaline 5 μg/ml | 12 | 152 ± 16 |

In experiments with anaesthetized dogs, S-1265 has been found to have effects equivalent to lidocaine and mepivacaine against arrhythmic heart-beats induced by ouabain, as can be seen from the results in Table 7:

TABLE 7

| Substance | Dose (mg/kg) | Number of animals | Number of regularized arrhythmias | Duration of regulation (min) |
|---|---|---|---|---|
| S-1265 | 1.0 | 6 | 4 (67%) | 120 ± 30 |
| | 2.0 | 6 | 5 (83%) | 200 ± 40 |
| Lidocaine | 1.0 | 20 | 12 (60%) | 135 ± 50 |
| | 2.0 | 24 | 19 (79%) | 220 ± 30 |
| Mepivacaine | 1.0 | 10 | 5 (50%) | 110 ± 20 |
| | 2.0 | 12 | 6 (50%) | 185 ± 50 |

In view of the results of the toxicity test, the substance N-(3-hydroxypropyl)pipecolinyl-2,6-dimethylanilide has considerably greater therapeutic potential than lidocaine or mepivacaine, both as a local anaesthetic and as an antiarrhythmic agent.

C. L-N-(2-hydroxyethyl)prolyl-2,6-dimethylanilide

L-N-(2-hydroxyethyl)prolyl-2,6-dimethylanilide (IX) herein sometimes referred to as S-1258 has been found to have an $LD_{50}$ value (iv) of 110 mg/kg (lidocaine 28 mg/kg and mepivacaine 31 mg/kg) in experiments with mice (NMRI, ♂ 22–25 g).

In experiments on conscious rats, S-1258 gave CNS effects (convulsions) when 130±10 mg/kg was administered intravenously (5.0 mg/kg/min; N=10). In parallel experiments, similar convulsions occurred when using 39±2 mg/kg (N=10) lidocaine and 38±3 mg/kg (N=10) mepivacaine.

In experiments on guinea-pigs, S-1258 proved to have better local anaesthetic effect than lidocaine after intracutaneous infiltration, as can be seen from the results in Table 8.

TABLE 8

| Substance | Concentration | Number of animals | Duration of anaesthesia (min) |
|---|---|---|---|
| S-1258 | 1.0% + adr. 5 μg/ml | 12 | 111 ± 8 |
| Lidocaine | 1.0% + adr. 5 μg/ml | 12 | 132 ± 7 |
| Mepivacaine | 1.0% + adr. 5 μg/ml | 12 | 152 ± 16 |

In experiments with anaesthetized dogs, S-1258 has been found to be effective against arrhythmic heartbeats induced by ouabain, as can be seen from the results in Table 9:

TABLE 9

| Substance | Dose (mg/kg) | Number of animals | Number of regularized arrhythmias | Duration of regulation (min) |
|---|---|---|---|---|
| S-1258 | 1.0 | 6 | 5 (83%) | 95 ± 20 |

TABLE 9-continued

| Substance | Dose (mg/kg) | Number of animals | Number of regularized arrhythmias | Duration of regulation (min) |
|---|---|---|---|---|
| | 2.0 | 6 | 4 (67%) | 195 ± 40 |
| Lidocaine | 1.0 | 20 | 12 (60%) | 135 ± 50 |
| | 2.0 | 24 | 19 (79%) | 220 ± 30 |
| Mepivacaine | 1.0 | 10 | 5 (50%) | 110 ± 20 |
| | 2.0 | 12 | 6 (50%) | 185 ± 50 |

In view of the results of the toxicity test, the substance L-N-(2-hydroxyethyl)prolyl-2,6-dimethylanilide has greater therapeutic potential than lidocaine and mepivacaine both as local anaesthetic and as antiarrhythmic agent.

D.
N(quaternary-2-hydroxyethyl-N-methyl)pipecolinyl-2,6-dimethylanilide

N(quaternary-2-hydroxyethyl-N-methyl)pipecolinyl-2,6-dimethylanilide (VIII) herein sometimes referred to as (N-methyl-S-1249) has been found to have an $LD_{50}$ value (iv) of 84 mg/kg (lidocaine 28 mg/kg and mepivacaine 31 mg/kg in tests performed earlier) in experiments with mice (NMRI, ♂ 20–24 g).

In experiments on conscious rats, N-methyl-S-1249 gave CNS side effects (convulsions) only after 125 mg/kg had been administered intravenously (5.0 mg/kg/min; N=10). In parallel experiments similar convulsions occurred when using 39±2 mg/kg (N=10) lidocaine and 38±3 mg/kg (N=10) mepivacaine.

In experiments on guinea-pigs, N-methyl-S-1249 was found to give local anaesthetic effect after intracutaneous infiltration, as can be seen from the results in Table 10:

TABLE 10

| Substance | Concentration | Number of animals | Duration of anaesthesia (min) |
|---|---|---|---|
| N-methyl-S-1249 | 1.0% + adr. 5 μg/ml | 12 | 128 ± 12 |
| Lidocaine | 1.0% + adr. 5 μg/ml | 12 | 132 ± 7 |
| Mepivacaine | 1.0% + adr. 5 μg/ml | 12 | 152 ± 16 |

In experiments with anaesthetized dogs, N-methyl-S-1249 has been found to have rhythm-regularizing effects against arrhythmic heart-beats induced by ouabain, as can be seen from the results in Table 11:

TABLE 11

| Substance | Dose (mg/kg) | Number of animals | Number of regularized arrhythmias | Duration of regulation (min) |
|---|---|---|---|---|
| N-methyl-S-1249 | 1.0 | 4 | 4 (100%) | 180 ± 30 |
| | 2.0 | 4 | 4 (100%) | 310 ± 50 |
| Lidocaine | 1.0 | 20 | 12 (60%) | 135 ± 50 |
| | 2.0 | 24 | 19 (79%) | 220 ± 30 |
| Mepivacaine | 1.0 | 10 | 5 (50%) | 110 ± 20 |
| | 2.0 | 12 | 6 (60%) | 185 ± 50 |

In view of its low toxicity, therefore, the substance N(quaternary-2-hydroxyethyl-N-methyl)-pipecolinyl-2,6-dimethylanilide has greater therapeutic potential than lidocaine or mepivacaine, particularly as a heart antiarrhythmic agent.

In clinical use the substances under consideration can be administered topically, perorally or parenterally, for instance by injection or by infusion in the form of one or more active components either in the form of a free base or as a pharmaceutically acceptable salt such as hydrochloride, lactate, acetate, sulphamate in combination with a pharmaceutically acceptable carrier or diluent. These pharmaceutical preparations are also included in the invention. The active component or components normally constitute(s) from 0.01 to 0.20 percent by weight of the pharmaceutical preparation.

Solutions for parenteral administration by injection can be prepared as liquid preparations of water-soluble, pharmaceutically acceptable salts of the active component or components. These solutions may also include stabilizing agents and/or buffers and/or agents which prolong or reinforce the biological effects of the active substance(s), such as catechol amines, vasocontracting agents, dextranes, surface active agents or stabilizing fat emulsions.

Preparation of rectal administration can be produced in the form of suppositories, lotions or gels containing the active substance(s) mixed with a neutral fat-base. The preparations may also be manufactured as gelatin capsules containing the active substance(s) mixed with a vegetable oil or paraffin oil. The rectal preparations may also contain substances to prolong or reinforce the biological effects of the active substance(s), such as vasocontracting agents, surface-active agents or steroids.

Preparations for topical administration can be manufactured as solutions, lotions or gels and these preparations may also include stabilizing agents and/or buffers and/or agents to prolong or reinforce the biological effects of the active substance(s), for instance alcohols, surface-active agents or vasocontracting agents.

We claim:

1. A compound of the formula

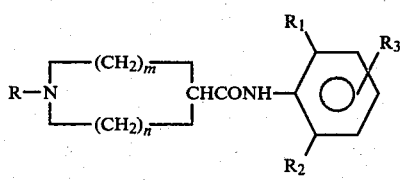

in which m and n are a pair of integers such that m=0 or 1 and n=3−m or m=0, 1 or 2 and n=4−m, R is straight or branched hydroxyalkyl having 2 to 4 carbons and having the hydroxy group in a terminal position, $R_1$ is selected from the group consisting of methyl and methoxy, $R_2$ is selected from th group consiting of methyl and ethyl and $R_3$ is selected from the group consisting of hydrogen and methyl; and pharmaceutically acceptable acid addition salts thereof and quaternary N-methyl halides and quaternary N-ethyl halides thereof.

2. A compound or salt according to claim 1 in which R is selected from the group consisting of 2-hydroxyethyl, 3-hydroxypropyl, 4-hydroxybutyl, 2-hydroxy-1-methylethyl and quaternary 3-hydroxy-1-methylpropyl-N-methyl-halide.

3. A compound according to claim 1 of formula

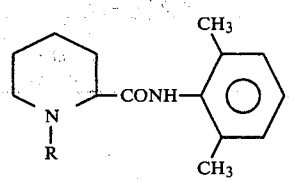

in which R is selected from the group consisting of 2-hydroxyethyl, 3-hydroxypropyl, quaternary 2-hydroxyethyl-N-methyl halide, quaternary 3-hydroxypropyl-N-methyl halide, quaternary 2-hydroxyethyl-N-ethyl halide, and quaternary 3-hydroxypropyl-N-ethyl halide; and a pharmaceutically acceptable salt thereof.

4. A compound according to claim 3 in which R is selected from a group consisting of 2-hydroxyethyl, 3-hydroxypropyl and quaternary 2-hydroxyethyl-N-methyl halide; and a pharmaceutically acceptable salt thereof.

5. A compound selected from the group consisting of N-(2-Hydroxyethyl)pipecolinyl-2,6-dimethylanilide, its pharmaceutically acceptable acid addition salts and its optically active stereoisomers.

6. A compound selected from the group consisting of N-(2-Hydroxyethyl)pipecolinyl-2,4,6-trimethylanilide, its pharmaceutically acceptable acid addition salts and its optically active stereoisomers.

7. A compound selected from the group consisting of N-(3-Hydroxypropyl)pipecolinyl-2,6-dimethylanilide, its pharmaceutically acceptable acid addition salts and its optically active stereoisomers.

8. A compound selected from the group consisting of N-(2-Hydroxyethyl)pipecolinyl-2-methoxy-6-methylanilide, its pharmaceutically acceptable acid addition salts and its optically active stereoisomers.

9. A compound selected from the group consisting of N-(4-Hydroxybutyl)isopipecolinyl-2,4,6-trimethylanilide, its pharmaceutically acceptable acid addition salts and its optically active stereoisomers.

10. A compound selected from the group consisting of N-(2-Hydroxy-methylethyl)-prolyl-2,6-dimethylanilide, its pharmaceutically acceptable acid addition salts and its optically active stereoisomers.

11. A compound selected from the group consisting of N-(Quaternary-2-hydroxyethyl-N-methyl)pipecolinyl-2,6-dimethylanilide, its pharmaceutically acceptable acid addition salts and its optically stereoisomers.

12. A compound selected from the group consisting of N-(2-hydroxyethyl)prolyl-2,6-dimethylanilide, its pharmaceutically acceptable acid addition salts and its optically active stereoisomers.

13. A compound according to claim 1 wherein the compound is in the form of an optically active stereoisomer.

14. A compound according to claim 2 wherein the compound is in the form of an optically active stereoisomer.

15. A compound according to claim 3 wherein the compound is in the form of an optically active stereoisomer.

16. A compound according to claim 4 wherein the compound is in the form of an optically active stereoisomer.

17. A local anesthetic composition containing as an active substance a locally anesthetic effective amount of a compound as claimed in claims 1, 2, 3, or 4 and a pharmaceutically acceptable carrier.

18. A composition according to claim 17 wherein the compound constitutes 0.01 to 40% by weight of the composition.

19. A method of producing local anaesthesia in mammals which comprises administering to the subject in need of such local anaesthesia a therapeutically effective dose of a compound as claimed in claims 1, 2, 3, 4, 5, 6, 7, 8, 9, 10, 11, 12, 13, 14, 15 or 16.

20. A method of producing topical anaesthesia in mammals which comprises administering to the subject in need of such topical anaesthesia a therapeutically effective dose of a compound as claimed in claims 1, 2, 3, 4, 5, 6, 7, 8, 9, 10, 11, 12, 13, 14, 15 or 16.

21. A method of treating heart arrhythmias in mammals which comprises administering to the subject in need of such treatment a therapeutically effective dose of a compound as claimed in claims 1, 2, 3, 4, 5, 6, 7, 8, 9, 10, 11, 12, 13, 14, 15 or 16.

22. A topical anesthetic composition containing as an active substance a topically effective amount of a compound as claimed in claims 1, 2, 3 or 4 and a pharmaceutically acceptable carrier.

23. An antiarrhythmic composition containing as an active substance an anti-arrhythmic effective amount of a compound as claimed in claims 1, 2, 3 or 4 and a pharmaceutically acceptable carrier.

* * * * *

UNITED STATES PATENT AND TRADEMARK OFFICE
CERTIFICATE OF CORRECTION

PATENT NO. : 4,302,465

DATED : November 24, 1981

INVENTOR(S) : Ekenstam et al.

It is certified that error appears in the above—identified patent and that said Letters Patent is hereby corrected as shown below:

Col. 1, line 53, "methylproply" should read --methylpropyl--;
Col. 1, lines 53-54, "hydroxyproply" should read --hydroxypropyl--;
Col. 1, line 55, "hydroxyproply" should read --hydroxypropyl--;
Col. 2, line 33, "COHN" should read --CONH--;
Col. 5, line 46, "an" should read --and--;
Col. 6, line 51, "reflux" should read --refluxed--;
Col. 7, line 24, "(5.0 mg/mg/min;" should read --(5.0 mg/kg/min;--;
Col. 7, line 31, "intracutinous" should read --intracutaneous--;
Col. 7, line 35, "irratated" should read --irritated--;
Col. 11, line 56, "th" should read --the--;
Col. 11, line 56, "consiting" should read --consisting--;
Col. 12, line 48, after "optically" insert --active--.

Signed and Sealed this

Eleventh Day of May 1982

[SEAL]

Attest:

GERALD J. MOSSINGHOFF

Attesting Officer

Commissioner of Patents and Trademarks

UNITED STATES PATENT AND TRADEMARK OFFICE
CERTIFICATE OF CORRECTION

PATENT NO. : 4,302,465

DATED : November 24, 1981

INVENTOR(S) : Ekenstam et al.

It is certified that error appears in the above—identified patent and that said Letters Patent is hereby corrected as shown below:

Column 11, line 8, "0.20" should be --20--;

Claim 18, "40" should be --20--.

Signed and Sealed this

Twenty-first Day of August 1984

[SEAL]

Attest:

Attesting Officer

GERALD J. MOSSINGHOFF

Commissioner of Patents and Trademarks

REEXAMINATION CERTIFICATE (157th)

United States Patent
AF Ekenstam et al.

[11] B1 4,302,465
[45] Certificate Issued  Jan. 24, 1984

[54] THERAPEUTICALLY ACTIVE, SUBSTITUTED PIPERIDINES AND PYRROLIDINES THERAPEUTIC COMPOSITIONS THEREOF AND METHODS OF USE THEREOF

[76] Inventors: Bo T. AF Ekenstam, Box 721, Hjälteby, Sweden, S-440 74; Gunnar A. K. Aberg, Utsiktsvägen 7, Falkenberg, Sweden, S-311 00

Reexamination Request:
No. 90/000,281, Oct. 26, 1982

Reexamination Certificate for:
Patent No.: 4,302,465
Issued: Nov. 24, 1981
Appl. No.: 97,148
Filed: Nov. 26, 1979

Certificate of Correction issued May 11, 1982.

[30] Foreign Application Priority Data
Oct. 7, 1979 [SE] Sweden .............................. 7906000

[51] Int. Cl.³ .................. A61K 31/445; C07D 213/56
[52] U.S. Cl. .................................... 424/267; 546/225; 548/337; 424/274
[58] Field of Search ....................... 546/225; 548/337; 424/267, 274

[56] References Cited
U.S. PATENT DOCUMENTS
2,792,399  5/1957  Ekenstam et al. .................. 546/225

OTHER PUBLICATIONS
Likhosherstov et al. "Khim. Farm. Zh" vol. 10, No. 7, pp. 36–41 (1976).

*Primary Examiner*—Robert T. Bond

[57] ABSTRACT

A compound of formula

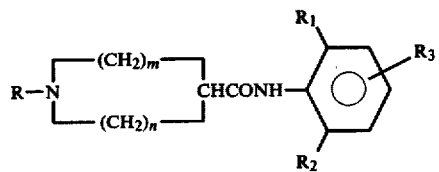

in which
  m and n are a pair of integers such that $m=0$ or 1 and $n=3-m$ or $m=0$, 1 or 2 and $n=4-m$, R is straight or branched $C_2$ to $C_4$ alkyl having a terminal hydroxy group,
  $R_1$ is methyl or methoxy,
  $R_2$ is methyl or ethyl and
  $R_3$ is hydrogen or methyl;
or a pharmaceutically acceptable salt thereof is provided, as well as compositions containing these compounds and processes for preparing them. The compounds can be used to produce topical and local anaesthetic effects in mammals and are also useful as heart anti-arrhythmic agents.

REEXAMINATION CERTIFICATE ISSUED UNDER 35 U.S.C. 307.

THERAPEUTICALLY ACTIVE, SUBSTITUTED PIPERIDINES AND PYRROLIDINES THERAPEUTIC COMPOSITIONS THEREOF AND METHODS OF USE THEREOF

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 6, lines 36–45:

EXAMPLE 4

The procedure of Example 1 or 2 is used to produce the optically active stereoisomers. The starting material is either the D(−)- or L(+)-amides instead of racemic, D,L-piperidine-α-carboxy-2,6-dimethylanilide. A final product corresponding to D(−)- or L(+)-N-(2-hydroxyethyl)-pipecolinyl-2,6-dimethylanilide hydrochloride is obtained and has an optical activity of $[\alpha]_D^{25}$ and ± [+] 19°5' for the D(−) and L(+) forms. The L(+) form has a melting point of [217°] *192–197* C. *The D(−) form has a melting point of 217° C.*

AS A RESULT OF REEXAMINATION, IT HAS BEEN DETERMINED THAT:

The patentability of claims 5, 7, 8 and 11 is confirmed.
Claims 6, 9, 10, and 12, having been finally determined to be unpatentable, are cancelled.

Claims 1 and 19-21 are determined to be patentable as amended:

Claims 2-4, 13-18, 22, and 23, dependent on amended claims, are determined to be patentable.

1. A compound of the formula

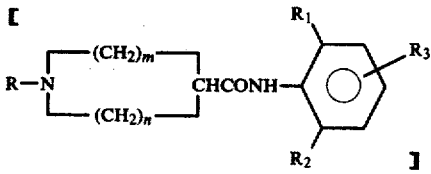

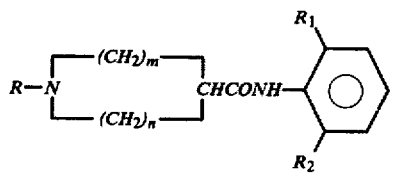

in which [m and n are a pair of integers such that m=0 or 1 and n=3−m or] m=0, 1 or 2 and n=4−m, R is straight or branched hydroxyalkyl having 2 to 4 carbons and having the hydroxy group in a terminal position, $R_1$ is selected from the group consisting of methyl and methoxy [,] *and* $R_2$ is selected from the group consisting of methyl and ethyl [and $R_3$ is selected from the group consisting of hydrogen and methyl]; and pharmaceutically acceptable acid addition salts thereof and quaternary N-methyl halides and quaternary N-ethyl halides thereof.

19. A method of producing local anaesthesia in mammals which comprises administering to the subject in need of such local anaesthesia a therapeutically effective dose of a compound as claimed in claims 1, 2, 3, 4, 5, [6, ] 7, 8, [9, 10,] 11, [12,] 13, 14, 15 or 16.

20. A method of producing topical anaesthesia in mammals which comprises administering to the subject in need of such topical anaesthesia a therapeutically effective dose of a compound as claimed in claims 1, 2, 3, 4, 5, [6,] 7, 8, [9, 10,] 11, [12,] 13, 14, 15 or 16.

21. A method of treating heart arrhythmias in mammals which comprises administering to the subject in need of such treatment a therapeutically effective dose of a compound as claimed in claims 1, 2, 3, 4, 5, [6,] 7, 8, [9, 10,] 11, [12,] 13, 14, 15 or 16.

* * * * *